United States Patent [19]

Davis et al.

[11] Patent Number: 5,453,522

[45] Date of Patent: Sep. 26, 1995

[54] COLORANT FOR USE IN BUSINESS RECORDING

[75] Inventors: Chester Davis, Springfield, Ohio; Ford P. Wilgis; Vernon J. Shiner, Jr., both of Bloomington, Ind.

[73] Assignee: Indiana University Foundation, Bloomington, Ind.

[21] Appl. No.: 308,972

[22] Filed: Sep. 20, 1994

[51] Int. Cl.$^6$ ............................................. C07C 211/54
[52] U.S. Cl. ........................ 552/114; 562/125; 564/315; 564/330
[58] Field of Search ................... 564/315, 330; 562/125; 552/114

[56] References Cited

U.S. PATENT DOCUMENTS

| | | | |
|---|---|---|---|
| Re. 30,797 | 11/1981 | Davis | 427/288 |
| Re. 30,803 | 11/1981 | Davis | 282/27.5 |
| 3,193,404 | 7/1965 | Davis | 117/38 |
| 4,321,207 | 3/1982 | Cesark | 552/114 |
| 4,632,987 | 12/1986 | Tsujimoto et al. | 552/114 |

OTHER PUBLICATIONS

District Court, D. Delaware; Scott Paper Company et al. v. Moore Business Forms, Inc. No. 77–199–JLL, Decided Sep. 5, 1984.

*Primary Examiner*—Richard L. Raymond
*Attorney, Agent, or Firm*—Woodard, Emhardt, Naughton Moriarty & McNett

[57] ABSTRACT

Bis-substituted methanes and undissociated methylene salts of the formula $(Am)_2Z$ wherein Am is bis-(1,4 dimethylaminophenyl) and Z is $CH_2$ or $CH^+X^-$ wherein $X^-$ is a suitable anion, all useful in the production of deeply colored cations of the formula $(Am)_2CH^+$. These deeply colored cations are in turn useful in making and using carbonless copy papers, as well as thermal copying papers for use with fax machines.

8 Claims, No Drawings

COLORANT FOR USE IN BUSINESS RECORDING

FIELD OF THE INVENTION

This invention relates to an intensely-colored blue-black colorant, methods for its formation and its use in recording.

BACKGROUND OF THE INVENTION

The use of colorless recording systems dates back to the 1880's when Thomas Edison proposed the use of leuco Malachite Green on electrolytic telegraphic recording papers. This proposal was, however, slow to develop and it was not until 1938–40 that Groak et al. proposed the use of iron salts plus gelatin to form a carbonless carbon paper for use in recording. This Groak system involved separate coatings on separate sheets, or two insulated coatings on the same sheet. Unfortunately, Groak's paper was too hygroscopic (humidity sensitive) and too printing insensitive for practical use.

In the next important development, B.K. Green and coworkers proposed the use of Malachite Green Lactone as suggested by E. Weitz's publication on color reactions on clay surfaces and the use of the analogous compound, Crystal Violet Lactone with an acid-clay coated receiving sheet to form a colored print. Both of these reactions employed an acid-base reaction in which contact with acid transformed the colorless oxy base to a colored cation. As a first step, Green et al. emulsified the colorless base of the dye in a non-polar oil such as chlorinated diphenyl in a hydrophyllic colloid such as a gelatin solution in water. The encapsulated oil was then coated onto the surface of a top sheet in contact with an acid-clay coated bottom sheet. Pressure on the top sheet, as by striking with a pen or typewriter key, forced an oil droplet containing the colorless base onto the clay-coated receiving sheet to form colored indicia by the formation of the colored salt at those places where the colorless base was pressed against the acid-clay surface. Recent modifications of the Green et al. system use a polymeric acid on the receiving sheet to form a colored salt which is not discharged by contact with water. The chief drawback of this system is that the generation of a local excess of heat under writing pressure degrades polymeric acid to allergy-causing decomposition products.

Almost all of the prior art carbonless copy paper colorants have been acid-base color formers; that is, they are weak dye bases which react with, preferably, colorless acids to give colored dye salts.

An improved carbonless copy paper was proposed by Davis in 1965 (see Davis, U.S. Pat. Nos. Re. 30,797 and Re. 30,803; see also Heinisch Zollingen, *Color Chemistry*, 2nd Edition, Weiheim, N.Y., 1991, pages 393–6; and Rave, *Ullman's Encyclopaediader Technischen Chemie*, 4th Edition, Vol. 23, page 381, Verlag Chemie Weinheim). Unlike the previous systems, the Davis system utilized the principle of a colorless, associated dye salt which became colored on dissociation, conveniently by contact with the electrical ionizing field present on an unfired clay surface. This electrical ionizing field caused the dissociation of selected salts of Michler's Hydrol, particularly an organic sulfinic acid salt, to yield blue-colored indicia which were stable to both light and humidity. Approximately $1,000,000,000 worth of forms were sold employing the Davis invention up to the time when the system was superceded by a system which employed a mixture of three colorless dyes (leuco bases) whose colored ions collectively formed black indicia when contacted with a polymeric acid-coated sheet. There is, however, a major drawback to this three dye system; to wit, the three dyes fade under light at different rates, yielding, in most cases, magenta-colored indicia after some period of time.

The Davis colorless dye salt dissociation system has, to date, not been used with a mixture of colorless dye bases to yield a black print, and could not be used in an acid-base system.

At the present time, as mentioned above, all colorless copy papers which yield a black print similar to a black carbon paper print use a mixture of 2 or 3 color formers. What has long been desired is a colorless copy system (or carbon-less carbon paper) which uses only a single color-former to yield indicia with an intense blue-black to black shade on a suitable receiving surface.

Presently, world-wide yearly sales of colorless copy papers approximates $6,000,000,000.

It is an object of this invention to provide carbonless copy papers which yield black or deep blue-black indicia when subjected to the pressure of a typewriter key or pen or pencil.

Another object of this invention is to provide a heat-sensitive recording system for use in FAX machines to form a light-stable black to blue-black copy of the original document.

It is a further object of this invention to provide novel color bases or associated salts which can be converted from colorless to black or deep blue-black colors by reaction with oxidizing agents or under ionizing conditions which are capable of dissociating such undissociated salts, to yield a deeply colored cation. Other objects of this invention will appear from the following specification.

SUMMARY OF THE INVENTION

In accordance with the above and other objects, this invention provides, in its initial aspect, novel compounds of formula (I) and novel cations of formula (II)

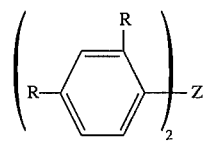

I

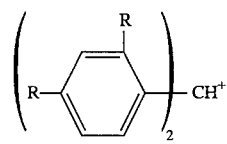

II wherein R is dimethylamino and Z is $CH_2$ (leuco base), or $CH^+X^-$ (undissociated salt) wherein $X^-$ is a suitable anion. Cations according to formula II above, are deeply-colored (black or blue-black) and are useful as dyes or colorants. It is to be understood that these deeply-colored cations are always accompanied in both aqueous and non-aqueous solutions by equal numbers of anions formed either during the oxidation of the leuco bases of formula I or by dissociation, under ionizing conditions, of the undissociated salts of formula I.

Salts of particular interest are the organic sulfinate salts where Z in I above is $CH^+X^-$ and X is $SO_2$—$R^1$ wherein $R^1$ is selected from the group $C_{1-8}$ straight-chain alkyl, phenyl or substituted phenyl wherein said substituents can be one or mole members of the class halo, lower alkyl, or lower alkoxy. These sulfinate salts readily dissociate under ionizing conditions, as for example, when the salt is contacted with an active clay coated paper. This dissociation yields the highly colored cation II. X-ray analysis shows a sulfonic structure; i.e. Z=CH—$SO_2$—R', for these salts, and it is understood that such structure, which dissociate on treatment with acid, are included within the term salt and the structure Z= $CH^+X^-$.

In a second aspect, this invention provides colored prints by contacting a solution of a leuco base (I when Z is $CH_2$) with a strong oxidant, thereby producing intensely colored indicia containing the cation II.

In a third aspect, this invention provides methods of printing whereby, by applying a solution of a sulfinate dye salt (FIG. I wherein Z is $CH^+X^-$ and $X^-$ represents an organic anion, particularly a sulfinate ion) to the surface of a receiving sheet having coated thereon a thin layer of a silicate capable of dissociating said sulfinate salt to yield the intensely colored cation II. In the above printing method, it is customary to have a first sheet coated on the reverse side with the solution of the leuco or associated dye salt and the solution is partly pressed onto the suitably-coated receiving sheet by the pressure of pen, pencil, typewriter key or the like. The result is black or deep blue-black printed or handwritten indicia which will neither fade nor change color for time periods of 6 months or longer.

In a fourth aspect, this invention provides a method of printing transmitted FAX copies whereby the colorless sulfinate dye salt combined with a heat-melting waxy vehicle is coated onto paper admixed with an ionizing silicate capable of dissociating said colorless sulfinate dye salt to yield the intensely colored cation II. In the above thermal printing method, application of a heated stylus melts the waxy vehicle onto the clay silicate-containing surface to provide a colored copy.

Finally, this invention provides a method of preparing compounds according to FIG. I above when Z is $CH^+X^-$ (preferably, X is $SO_2R^1$) which comprises reacting a solution of a 1,3-dimethylaminobenzene with a trialkyl orthoformate in the presence of sulfuric acid and an organic solvent, preferably 2,2,2-trifluoroethanol, to give the triarlymethane. The triarylmethane thus formed in turn reacts with an organic sulfinic acid to yield the undissociated colorless dyesalt (I where Z is $CH^+X^-$) plus 1,3-dimethylaminobenzene.

DISCLOSURE

The intensely-colored cation (II) of the present invention is obtained from fully methylated m-phenylene diamine (N,N,N'N'-tetramethyl-m-phenylenediamine). The corresponding derivates of o- and p-phenylenediamine are not suitable for use in the present invention. The preferred embodiment of the present invention is the generation of the intensely-colored cation (II above) by dissociation of the colorless associated sulfinic acid salt (III below).

The cationic colorant (II) can be prepared according to several procedures, one of which is new to the art. This novel procedure involves the reaction of N,N'-fully methylated m-phenylenediamine with methyl orthoformate to yield the triaryl leuco (IV). In the presence of a sulfinic acid in a suitable mutual solvent, this triarylmethane loses one aryl group to yield the cation plus N,N,N'N'-tetramethyl-m-phenylenediamine which can be recovered and recycled.

The thus formed cation immediately reacts with the sulfinic acid present in excess to yield the associated, colorless salt (where Z is $CH_2^+(R'SO_2)^-$.

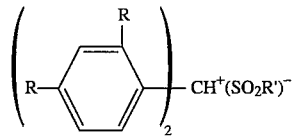

III

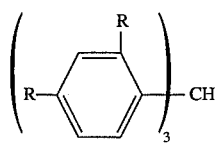

IV wherein R is dimethylamino and $R^1$ is phenyl or substituted phenyl wherein said substituents can be 1–3 members of the group lower alkyl, lower alkoxy or halo). The term "lower alkyl" means alkyl groups from 1–3 carbons.

Another procedure which can be used to generate the colored cation II involves the oxidation of the methane base (I wherein Z is $CH_2$). All of the colorless intermediates (I, III and IV) and the colored cation (II) are novel.

The reaction product of N,N,N',N'-tetramethyl-m-phenylenediamine (V) with methyl orthoformate was orginially thought to be the hydrol (I where Z would be CHOH); then it was thought that the product might be a bis-benzhydryl ether. X-ray analysis, however, revealed that the structure was in fact the triaryl methane (III). X-ray analysis of the toluenesulfinate salt (I where Z is $CH^+SO_2Tosyl$) proved that the assigned structure was indeed correct.

The starting material N,N,N',N'-tetramethyl-m-phenylenediamine is not currently commercially available. It is readily prepared, however, by the reaction of m-phenylenediamine with trimethylphosphate, using an improvement over the literature method of Thomas et al., J.Am.Chem.Soc. 68 895 (1946), which makes use of a high-boiling, water-soluble polar solvent In the work-up of the reaction which is exothermic since it contains unreacted trialkylphosphate.

SPECIFIC EMBODIMENTS OF THE INVENTION

Example 1

Preparation of N,N,N',N'-Tetramethyl-m-Phenylenediamine

A reaction mixture consisting of 200 g (1.85 mol) of m-phenylenediamine, 691 g (4.93 mol) of trimethyl phosphate and 400 g of ethyleneglycol was placed in a 5-liter-3-neck round bottomed flask fitted with a reflux condenser, thermometer and a dry nitrogen gas inlet tube. The mixture was stirred magnetically while being heated in the range 150°–60° C. using a heating mantle. At about 160° C., a vigorous exothermic reaction set in and the reaction flask temperature rose to about 210° C. The vigorous reaction gradually subsided after about 20 minutes. The reaction mixture was next heated to reflux temperature for about 6 hours. The reaction mixture was then cooled to a temperature in the range 60°–80° C. A solution of 7.4 molar NaOH (592 g NaOH; 14.8 mol) was carefully added with stirring to the reaction mixture. After the addition of the base had been completed, the neutralized reaction mixture was cooled to room temperature in order to allow any sodium phosphate formed to precipitate. The light-to-dark brown oily reaction product was layered on top of the aqueous phase. 200–300 ml of diethyl ether were then added and the contents of the flask filtered by suction using a sintered glass tunnel. The filtered salt was washed several times with 100 ml portions of ether and the ether washes added to the filtrate. The combined filtrates were placed in a separatory funnel and the ether layer separated. The aqueous layer was extracted with a 300 ml portion of ether and the ether wash combined with the ether extract. The ether layer was next washed with 300 ml of 5% aqueous potassium carbonate, the aqueous wash discarded and the ethereal solution dried over anhydrous potassium carbonate. The ether was removed in a rotary evaporator. vacuum distillation of the residue yielded 239 g of a clear liquid (yield=78%) comprising purified N,N,N', N'-tetramethyl-m-phenylenediamine; B. P.=55°–57° C. (0.01–0.02 mm. Hg).

N,N-dimethyl-N',N'-diethyl-m-phenylenediamine and N,N,N',N'-tetraethyl-m-phenylenediamine were prepared in the same manner using triethylphosphate.

Example 2

Preparation of Bis-(2,4-Dimethylaminophenyl) Methane

A reaction mixture containing 30.0 g of N,N,N',N'-tetramethyl-m-phenylenediamine, 75 ml of water and 15.5 ml of 12N HCl (0.187 mol) was placed in a 500 ml round-bottomed flask fitted with a dry nitrogen intake tube and a dropping funnel. The mixture was magnetically stirred until the diamine dissolved (about 10 minutes), at which time 10 ml of a 38% formalin solution was added dropwise over a period of about 15 minutes. The clear light yellow solution turned a brilliant orange and remained so during the course of the reaction. The reaction mixture was stirred at ambient temperature for an additional 9 hours. At this point, a $^{13}$C NMR of a sample of the reaction mixture showed that the desired product was present in a greater than 95% yield. The reaction mixture was then made basic by the addition of 9.0 g (.2225 mol) of NaOH. The desired product separated as a white emulsified liquid. 100 ml of methylene chloride were added to the emulsified liquid and, after stirring, the resulting mixture was transferred to a separatory funnel. The methylene chloride layer was separated, and the aqueous layer extracted with an additional portion of 100 ml of methylene chloride. The combined layers were dried over anhydrous potassium carbonate, filtered and the solvent removed in vacuo. The residue, comprising 30 g of the compound of the title (yield= 95.6%) was an orange glassy solid. A $^{13}$C NMR spectrum revealed that the product was at least 95% pure.

Example 3

Preparation of Deeply-Colored Cation II

A 3% xylene solution of the methane base from Example 2 was applied to a surface coated with chloranil (an oxidizing agent). An immediate black color was formed, comprising cation II.

The same solution was applied to a paper coated with a 50—50 mixture of chloranil and kaolin clay. An immediate black color was formed, again comprising cation II.

The black cation can be converted back to the colorless carbinol base and separated from the now-reduced chloranil-phenol form by the action of an acetone-alkali solution.

Example 4

Preparation of Tris-(2,4-Dimethyaminophenyl) Methane (III)

The most convenient way to prepare cation II for condensation with the sulfinic acid free from lead contamination is to condense the starting N,N,N',N'-tetramethyl-m-phenylenediamine from Example 1 with trimethyl orthoformate to yield the easily purified triaryl leuco IV. The triarylmethane derivative is obtained in excellent yield and with high purity, and can be converted to the preferred sulfinic acid salt of cation II in good yield as follows:

A reaction mixture containing 300 ml of distilled 2,2,2-trifluoroethanol and 90 g (0.54 mole) of N,N,N',N'-tetramethyl-m-phenylenediamine was placed in a 1 l. round-bottomed flask fitted with a dry nitrogen gas inlet tube and a reflux condenser connected to a gas bubbler. The solution was heated to about 50° C. by an oil bath. When temperature equilibrium was obtained, 14.4 ml of concentrated sulfuric acid (0.261 mol) were added. Heating at about 50° C. was continued while 116.5 g (1.096 mole) of trimethyl orthoformate were added in dropwise fashion over a period of about 1.5 hour. Within one minute after the initiation of the addition, the reaction mixture became a dark opaque blue-black color indicating that the cation II had been formed. After heating for about 6.5 hours, the reaction mixture was cooled by removal of the heating bath. As the solution was cooling, 100 ml of water were added (to react with any unreacted orthoformate present); and the resulting solution was stirred for an additional 20 minutes. Next, 200 ml of 2.75 M NaOH were added via the dropping funnel; and, after vigorous stirring, the blue-black color of the initial solution changed to a greenish-black color with a granular precipitate appearing on the walls of the flask. The contents of the flask were transferred to a one liter round-bottomed flask and concentrated by rotary evaporation in vacuo. After removal of all trifluoroethanol and any unreacated trimethyl orthoformate by the evaporative process, an additional 200 ml of 5% aqueous potassium carbonate were added. Rotary evaporation was resumed and continued until the contents of the flask had a volume in the range of 2–300 ml. Tris-(2,4-dimethylaminophenyl)methane (III) thus prepared was a lumpy orange-brown solid. After cooling the contents of the flask to room temperature, 100–200 ml of diethyl ether were added; and, after vigorous shaking, the ethereal-aqueous mixture was allowed to stand for about ½ hour. The bulk of the product separated as a solid which was collected by filtration using a sintered glass funnel. The reddish-brown solid thus obtained was rinsed with an additonal 100–200 ml portion of diethyl ether followed by 4–5 rinses with 200 ml portions of 5% aqueous potassium carbonate solution. The filter cake, comprising tris-(2,4-dimethylaminophenyl)-methane, now had a light green to light yellow color. The filter cake was air-dried at room temperature in a stream of dry air; wt.=85–96 g; yield= 89–100%; m.p.=184°–9° C. Recrystallization of the product from cyclohexane (xylene can also be used) gave 70–78 g of purified product; yield= 73.7–82.]%; m.p.= 192°–3° C.

X-ray analysis indicated that the structure of the compound produced by the above procedure was indeed tris-(2, 4-dimethylaminophenyl)-methane (III).

Example 5

Preparation of the p-Toluene Sulfinate Salt of Bis-(2,4-Dimethylaminophenyl)-Methylcarbonium Ion (Cation II)

Into a one 1. 3-neck round-bottomed flask were placed 50 g (0.1 mol) of the triaryl methane (III) from Example 4 and 350 ml of benzene. The flask was fitted with an inlet tube for admitting anhydrous nitrogen, a reflux condenser and a mechanical starter. The reaction mixture was heated by an oil bath while being stirred to a temperature of about 40° C. After 15–30 minutes, all of the triarylmethane had dissolved. 19.9 g of anhydrous sodium sulfate were added to the stirred solution to remove water formed in the above reaction. Next, 20.8 g (0.133 mol) of p-toluenesulfinic acid and 250 ml of benzene were placed in a 500 ml Erlenmeyer flask and the mixture heated at 40° C. with stirring until all of the acid had dissolved. This solution was then added to the benzene solution of the triarylmethane via the dropping funnel. The resulting mixture was continuously stirred at about 40° C. for three hours. Probes of the reaction mixture indicated that the reaction to form the toluenesulfinate salt was 95% complete after about 135 minutes.

The warm solution was then filtered to remove the drying agent and the resulting filtrate concentrated on a rotary evaporator. When the benzene had nearly all been removed, a light tan solid began to appear. Complete removal of the benzene yielded 70 g of a mixture of products. $^{13}$C NMR analysis indicated that the mixture consisted of about 80% of the desired p-toluenesulfinate salt of cation II and 20% of 2,4-dimethylaminobenzene which had split off in the presence of p-toluenesufinic acid (and can be recovered for reuse). Several recrystalizations of the sulfinate salt of cation II from a 7-3 hexane-toluene solvent mixture gave 25 g of purified salt (approximately 50% yield); m.p.=133°–5° C. The $^{13}$C NMR spectrum and X-ray crystal analysis of the recrystalized product were both consistent with the assigned structure for the desired p-toluenesulfone.

Analysis:

Calc. for $C_{28}H_{38}N_4O_2S$: C, 67.98; H, 7.74; N, 11.33; S, 6.48

Found: C, 68.13; H, 7.82; N, 11.22; S, 6.58

Example 6

Preparation of p-Toluenesulfinic Acid

The p-toluenesulfinic acid used in Example 5 was prepared as follows: 10% aqueous sulfuric acid was added in dropwise fashion to a saturated solution of sodium p-toluenesulfinate until precipitation of the free acid was complete. This precipitate was filtered by suction using a sintered glass funnel, and the resulting precipitate washed with several portions of cold water. The precipitate was then air-dried by sucking dry air through the funnel holding the precipitate for from 1–2 hours. The precipitate was then dissolved in diethyl ether, the ethereal solution dried over anhydrous calcium sulfate, the drying agent removed by filtration, and the filtrate concentrated in vacuo. p-Toluenesulfinic acid crystallized on chilling and the resulting crystals were separated by filtration and dried. p-Toluenesulfinic acid thus prepared melted at 55°–7°.

Example 7

Preparation of 2,4-Dimethylbenzene Sulfinate Salt of Cation II

About 7 g (14.1 mmol) of tris-(2,4-dimethylaminophenyl) methane were dissolved in 50 ml of benzene in a 250 ml 3-neck round-bottomed flask equipped with dry nitrogen inlet tube, reflux condenser and stirring means. The reaction mixture was heated at about 40° C. with an oil bath until all of the triaryl methane had dissolved. Next, 2.82 g (19.1 mmol) of sodium sulfate were added followed by 3.32 g (19.5 mmol) of freshly-prepared 2,4-dimethylbenzenesulfinic acid (2,4-Xylenesulfinic acid). The reaction mixture was heated at about 40° C. for about 1 hour after which time it was gravity-filtered, and the dark indigo blue lilt rate was concentrated in a rotary evaporator, resulting in a viscous blue glassy precipitate weighing 10 g $^{13}$C NMR analysis of the crude product revealed that it was a mixture of the desired sulfone plus a second product which, on analysis after purification, proved to be N,N,N',N'-tetramethyl-1,3-phenylenediamine. The blue glassy residue was dissolved in a minimal amount of diethyl ether, and the ethereal solution concentrated in a rotary evaporator. An off-white (partly beige) material (6.4 g) crystallized, was collected by filtration and air-dried. $^{13}$C NMR analysis indicated that this material was the 2.4-xylenesulfinic acid salt of cation II The material melted at 140°–2° C.; yield= 85.8%.

All of the sulfinate salts of the colored cation II have satisfactory solubility in the recording fluids employed in the present invention, even the benzenesulfinate salt (prepared according to the above procedures; mp=121°–3° C. with decomposition) is soluble enough for recording purposes. The preferred salts, however, are the p-toluenesulfinate and the 2,4-xylenesulfinate salt.

As previously stated, the preferred embodiments of this invention for production of colored cations are the stable colorless associated sulfinate salts. When one of these salts is contacted with a receiving surface comprising an ionizing clay, an immediate dissociation of the salt occurs to produce a black color. When the force contacting the undissociated salt is a pen, pencil, typewriter key or the like, black indicia are recorded on the receiving sheet. These black indicia are more stable to sunlight than the currently used three-color black indicia referred to previously. Black indicia on clay, formed by the processes of this invention, faded somewhat but were still clearly legible after 4.5 months of exposure. The black print on a receiving sheet of one commercial carbonless copy paper exposed side by side with a paper containing indicia of this invention was a faint pink and barely visible. Black indicia formed from cation II or other black-colored cations of this invention are stable under Indoor use and are eminently suitable for use for business documentation.

The original clay-coated receiving sheet used in the practice of this invention utilized a starch binder to retain the clay on the paper surface. This binder proved to be unsuitable and could be replaced by various polymeric emulsions. Binder compositions of from 20–100% (the amount employed is not critical) were tested. These included (1) a vinylacetate homopolymer, (2) a vinyl-acrylic copolymer, (3) a styrene-acrylic copolymer, (4) a styrene-butadiene copolymer and (5), an acrylic polymer. All bound clay to paper satisfactorily and did not interfere with color formation. However, we prefer the vinyl acetate polymer or the vinyl-acrylic copolymer. These binders were used with a series of unfired ionizing clays, such as attapulgite, bentonite and kaolinite.

Example 8

Color Development on Clay-Coated Paper

A 2.5% solution of bis-(2,4-dimethylaminophenyl)-methyl benzenesulfinate (a colorless, associated salt) in dibutyl phthalate was applied to a receiving sheet coated with attapulgite clay. An immediate, intense black color developed. The developed color had good light-stability and was still readable 6 months later. In the same fashion, a 3% solution of the above benzenesulfinate salt in xylene was applied to a receiving sheet comprising a kaoline coated paper. An immediate black color developed.

In the same fashion, a 3% solution of the p-toluenesulfinate salt of cation II in dibutyl phthalate was applied to an attapulgite clay-coated paper receiving sheet. An immediate intense black print developed. The print had good light stability. In indoor light, there was no appreciable fading after 6 months. After exposure to sunlight (under a glass cover) for 4.5 months, there was some fading but the print itself was still clearly legible. In contrast, a black print using a commercially available paper had faded badly to a very faint pink during this time period, and the print was largely undecipherable.

In the same fashion, a 3% solution of the 3,4-dimethylbenzenesulfinate salt (associated) of cation II was applied to a kaolin coated receiving sheet. An immediate intense black color appeared.

Example 9

Use of Emulsions containing Undissociated Salts of Cation II

A 3% solution of the above p-toluenesulfinate salt in dibutyl phthalate was emulsified in water using a small quantity of a standard detergent. A white emulsion resulted. A small amount of a hot gelatin solution (equal to 10% of the amount of dibutyl phthalate present) was added and dispersed in the white emulsion by shaking. This emulsion was then coated on a paper sheet, and the coated sheet air dried. The dried sheet was placed in contact with an attapulgite clay coated receiving sheet. Pressure, as by a stylus, applied to the back of the sheet coated with the emulsion gave intense black colored indicia on the receiving sheet.

A 3% solution of the 2,4-xylenesulfinate salt (associated) of colored cation II was applied to a paper coated with attapulgite clay in a polymer emulsion binding of the type described above. An immediate intense black color (cation II) was obtained.

The recording system described above can also be adapted for use in heat-recording systems for use in FAX machines and the like. Initially, a solution of the dye salt in hot wax was prepared and this solution emulsified in hot water for application to a paper surfae. Surprisingly, it was found that extensive decomposition of the dye salt occurred during the emulsification process, possibly caused by "cavitation" effects when a blender was used to effect emulsification. To avoid such decomposition, the solid dye salt was ground and the finely-divided salt added to a mixture of finely-divided wax and finely-divided clay. The mixture, plus a polymeric emulsion binder, was coated on paper. The purpose of the binder was to help the mixture adhere to the paper. Application of heat to the coated paper caused the wax to melt thereby dissolving the dye salt which dissociated immediately to yield the intensely colored cation before the wax could resolidify. These processes are more fully illustrated in the following specific example.

Example 10

Use of Wax Emulsions in Coating Paper for Use in Fax

Ten grams of refined vegetable wax (refined Carnauba or Ouricury) was finely divided and then mixed with 0.3 g of finely-divided 3,4-xylenesulfinate salt of cation II. A wet slurry of 19 g of attapulgite clay (or other suitable ionizing clay) in 75 g of water was added to the previous mixture followed by 5 g of an emulsion of a polymeric binder (as described above) with gentle stirring. The resulting mixture was coated onto paper and the coated paper air-dried at room temperature, resulting in an off-white coated paper. Application of a heated stylus to the surface of the coated paper served to melt the wax, thus dissolving the dye salt. The solution of the dye salt was at the same time exposed to the clay. The dye salt immediately dissociated, yielding black indicia. This type of recording system yields a heat-sensitive recording paper suitable for use in current FAX systems.

In the same fashion, a 10 g sample of refined monton wax was placed in a 125 ml Erlenmeyer flask and the wax melted on a hot plate. The mouton wax was emulsified in hot water at a temperature of about 95° C. using a Waring Blender. Ten grams of kaolin clay were added and the wax absorbed onto the surface of the clay. Ice was added to chill the emulsion and solidify the wax. To the admixture of wax and clay were added 0.3 g of the finely divided p-toluenesulfinate salt of cation II plus about 5 g of a polymer emulsion (as described above) while the mixture was being gently stirred. The resulting mixture was carefully coated onto paper and the coated paper air-dried. Application of a heated stylus to the surface of the coated paper melted the wax. The now liquid wax dissolved the associated dye salt which practically simulltaneously dissociated as its solution in wax contacted the clay surface. Black colored indicia appeared immediately where the heated stylus touched the coated paper. This type of recording system is also useful in FAX machines.

For certain carbonless copy papers, finely-divided dye salt admixed with an ionizing clay can be used with an encapsulated solvent to yield a colorless surface. Frictional writing pressure releases the solvent which thereupon dissolves the associated dye salt. When this solution contacts the clay surface at those points of friction (where the writing pen or type contacts the coated paper), intense black indicia are produced.

It should be clearly understood that the present invention is not limited to the specific examples used for illustrative purposes only. The various recording fluids disclosed could also be encapsulated with a hard coating, mixed with clay and applied to the paper to form a self-recording copy paper. Furthermore, variations in the methods disclosed for preparing the sulfinate salts of the present invention would be obvious to those skilled in the art and are therefore equivalent to the methods disclosed herein.

We claim as our invention

1. A compound of the formula

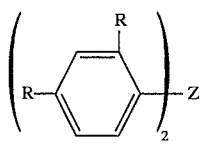

wherein each R is dimethylamino and Z is $CH_2$, or $CH^+X^-$ wherein $X^-$ is an anion.

2. A salt according to claim 1 capable of forming an intensely colored cation upon dissociation when contacted with acid wherein Z is $CH^+X^-$ and $X^-$ is an anion derived from an acid-dissociatable salt.

3. A salt according to claim 2 wherein the anion $X^-$ is an organic sulfinate.

4. A salt according to claim 3 wherein the anion is an organic sulfinate of the formula $R^1\text{-SO}^-$ wherein $R^1$ is selected from the group $C_{1-8}$ straight-chain alkyl, phenyl or substituted phenyl wherein said phenyl substituents can be one to three members of the group lower alkyl, lower alkyloxy and halo.

5. As a new composition of matter, an intensely colored cation of the formula

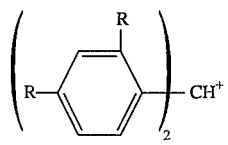

wherein each R Is dimethylamino.

6. A leuco base according to claim 1 wherein Z is $CH_2$.

7. The method of preparing a compound of the formula

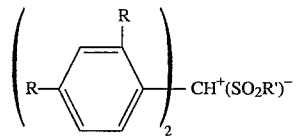

wherein each R is dimethlamino and wherein R is $C_{1-8}$ straight-chain alkyl, phenyl or substituted phenyl wherein said substituents can be one to three members of the group lower alkyl, lower alkoxy and halo, which comprises reacting a solution of a tris (2,4-dimethylaminophenyl)-methane of the formula

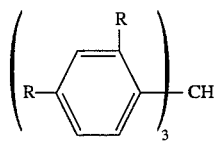

wherein each R is dimethylamino with a solution of an organic sulfinic acid, $R^1SO_2H$, whereby the sulfinate salt of the cation

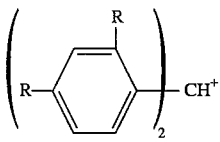

is formed, wherein each R is dimethylamino.

8. A compound of the formula

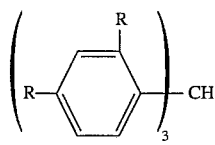

wherein each R is dimethylamino.

* * * * *

UNITED STATES PATENT AND TRADEMARK OFFICE
CERTIFICATE OF CORRECTION

PATENT NO. : 5,453,522
DATED : September 26, 1995
INVENTOR(S) : Chester Davis; Ford P. Wilgis; Vernon J. Shiner, Jr.

It is certified that error appears in the above-indentified patent and that said Letters Patent is hereby corrected as shown below:

```
In col. 3, line 3, please change "mole" to --more--.
In col. 4, line 41, please change "In" to --in--.
In col. 5, line 5, please change "tunnel" to --funnel--.
In col. 5, line 15, please change "vacuum" to --Vacuum--.
In col. 6, line 64, please change "82.]%" to --82.1%--.
In col. 7, line 12, please change "starter" to --stirrer--.
In col. 8, line 17, please change "lilt rate" to --filtrate--.
In col. 8, line 28, please insert a period after "II".
In col. 8, line 54, please change "Indoor" to --indoor--.
In col. 9, line 13, "In" should start a new paragraph.
In col. 11, line 36, please change "Is" to --is--.
In col. 12, line 1, please change "R", second occurrence, to
-- R¹--.
```

Signed and Sealed this

Seventeenth Day of September, 1996

Attest:

BRUCE LEHMAN

*Attesting Officer*     Commissioner of Patents and Trademarks